(12) United States Patent
Abreu (10) Patent No.: US 7,957,804 B2
(45) Date of Patent: Jun. 7, 2011

(54) NON-INVASIVE BATTERY RECHARGER FOR ELECTRONIC CARDIAC IMPLANTS

(76) Inventor: António Manuel Sequeira Abreu, Carregado (PT)

( * ) Notice: Subject to any disclaimer, the term of this patent is extended or adjusted under 35 U.S.C. 154(b) by 289 days.

(21) Appl. No.: 12/091,787

(22) PCT Filed: Oct. 25, 2006

(86) PCT No.: PCT/PT2006/000025
§ 371 (c)(1), (2), (4) Date: Apr. 28, 2008

(87) PCT Pub. No.: WO2007/049983
PCT Pub. Date: May 3, 2007

(65) Prior Publication Data
US 2008/0269828 A1    Oct. 30, 2008

(30) Foreign Application Priority Data
Oct. 28, 2005   (PT) .......................... 103374

(51) Int. Cl.
*A61N 1/00* (2006.01)
(52) U.S. Cl. ....................................... 607/33
(58) Field of Classification Search .................. None
See application file for complete search history.

(56) References Cited

U.S. PATENT DOCUMENTS

| 3,766,463 | A | * | 10/1973 | Ruben | 320/143 |
| 5,314,457 | A | | 5/1994 | Jeutter et al. | 607/116 |
| 5,704,351 | A | | 1/1998 | Mortara et al. | 128/630 |
| 6,442,434 | B1 | | 8/2002 | Zarinetchi et al. | 607/61 |
| 6,516,227 | B1 | * | 2/2003 | Meadows et al. | 607/46 |
| 2003/0040291 | A1 | | 2/2003 | Brewer | 455/127 |
| 2004/0039423 | A1 | | 2/2004 | Dolgin | 607/27 |
| 2007/0167879 | A1 | * | 7/2007 | Cochran | 600/595 |

FOREIGN PATENT DOCUMENTS
GB    1 492 990    11/1977

OTHER PUBLICATIONS

PCT/PT2006/000025, International Search Report, Herbert Schoeffmann, Jan. 25, 2007.

* cited by examiner

*Primary Examiner* — Mark W Bockelman
*Assistant Examiner* — Elizabeth K So
(74) *Attorney, Agent, or Firm* — Joseph T. Guy; Nexsen Pruet, LLC (57) ABSTRACT

The present invention refers to a device used to recharge the battery of electronic cardiac implants, like implanted pacemakers and defibrillators. It can be used to recharge the battery after an emergency requirement, such as: defibrillation or in diagnosis and or reprogramming of implants, during which no energy is demanded from the internal battery, seeing that the energy feed becomes guaranteed (accepted) by the proposed device. The invention is composed by three essential components: a generator (A), a transmitter unit (B) and a receptor coil (C). The generator is destined to produce an energy signal with determined amplitude and frequency and that is carried across through a coaxial cable to the transmitter unit (B). The emitted magnetic field is captured by the receptor coil (C) that is implanted inside the human body, generating a voltage with the absence of the Gibbs phenomenon. Furthermore, the battery recharging device guarantees the energetic supply of a communication channel between the exterior for diagnosis and/or implant reprogramming. In this case, there will be no demand of energy from the internal battery.

7 Claims, 9 Drawing Sheets

NON-INVASIVE BATTERY RECHARGER FOR ELECTRONIC CARDIAC IMPLANTS

The present invention turns possible the battery recharging of cardiac implants, like implanted pacemakers and defibrillators, allowing a longer life for the internal battery in the human body, and postponing the customary chirurgic intervention for replacement.

The energy consumption of the cardiac implants varies according to its function, this being determined by the pathology and activity of the patient.

The duration of the cardiac implant battery varies from 3 to 9 years, being essentially determined by the electrical energy consumption.

The electrical energy consumption, not considering the scale factor referring to the voltage amplitude, is proportional to the product between the medium electrical current value and the interval of time during which the same persists. This product characterises the electrical charge that moves from the battery to the implant's electronic circuit.

During the progress that accompanies the scientific investigation in the medical and in the electronic fields more and more sophisticated implants are emerging, in terms of functionality and in signal processing speed.

The assisted reprogramming, the defibrillation and periodic monitoring of the implant activity are some of those potentials.

The proposed configuration offers the possibility to access and change the implant's functionality algorithmic structure, without energy consumption of the internal battery, since the energetic supply is now guaranteed by the proposed device.

Actually there is no known process that permits the recharge of the battery. One of the prevention factors to achieve the energetic transfer to the implant's interior through a non-invasive process is the great distance that separates the implant from the exterior transmitter.

To overcome this obstacle in nowadays technology there are solutions based on switched power supplies which basic functionality principle is set on the impulse modulation technique (PWM—pulse width modulation). In these types of sources the form of voltage outgoing wave is affected by the variation of the width of the impulse.

However, this technique is associated to an effect known as the Gibbs phenomenon: it consists in an increased importance of the high-frequency electromagnetic noise in the, which can be quantified by Fourier analysis.

This high-frequency electromagnetic noise is detected by the implants electronic circuits, resulting in data/signal misinterpretation and/or erroneous decisions resulting from the algorithmic implants processing, with the obvious consequences for the patient.

It is precisely these inconveniences that characterise the actual state of the technique. Or else let us observe:

Reference US2005075696 refers to the use of an oscillatory current which will induce a voltage to the terminals of a secondary coil, not specifying which and not considering the electromagnetic interferences effect.

References US2005037256 and FR2420832 does not comment about the primary current, referring only to the use of a diode in the net (169) and (6), respectively, which represents poor energy efficiency for each cycle of the secondary voltage. In this case, a full wave rectification could be used, instead of the half-wave rectification.

Proposal DE2720331 is similar to the ones described in the above paragraph. However, it shows an inaccuracy in the schematic in the diode (6) and/or battery (2) polarity.

Reference JP2002315209 does not specify the waveform of the primary voltage and, from the presented schematic, the production of EMI noise is not excluded.

The same applies to reference U.S. Pat. No. 5,411,537, which also does not predict the primary voltage wave form.

On the other hand, the proposal EP0473957 presents a solution that does not consider the Gibbs phenomenon, besides the evidence of the necessity to use the detector (84), to measure phase difference or frequency difference. In this way, this proposal admits the existence of frequency components distinct form the fundamental.

The Prototype described in FIG. 1a of in Reference GB1419531 presents an efficient solution to process the full period of the secondary voltage, using the rectifier bridge (30), the sensing resistor (32) and the FET (31). However, from the auxiliary coil we verify that the frequency control of the energy carrier signal (which is also not specified, as in the above examples) is determined by the pacemaker with a tuned receptor excited by the coil (20b).

Summarising, the conceptions which characterise the state of the art does not attend to the Gibbs phenomenon. Consequently, the electronic unit of the implant is exposed to unacceptable EMI levels.

The present invention is composed by three essential components: a generator, a transmitter unit and a coil receptor.

Besides that, it does not need any feedback network for the process control, simplifying its use.

This invent does not permit the appearance of the Gibbs phenomenon, since the energy signal carrier wave is (co) sinusoidal and the supplied resonant network is linear. Thus, the effect of eventual electromagnetic interferences does not apply since the energy carrier signal as a known and allowed frequency in the communication channel.

Nevertheless, the utilisation of the sinusoidal signals contributes to the appearance of the reactive components of the electrical currents coming from the resonance network. Consequently, a supplemental dissipative effect occurs at the output power circuit of the generator and an increase of the energy consumption, representing less efficiency of energy transfer.

The form found and explored to overcome this problem consists in minimising the flow of reactive energy circulating in the resonant network.

By minimizing the reactive energy transit, a reduction/exclusion of the output current reactive component is achieved, resulting in less power dissipation—Joule effect—in the generator stage. In these conditions the resonant network is purely resistive.

Figure 1:
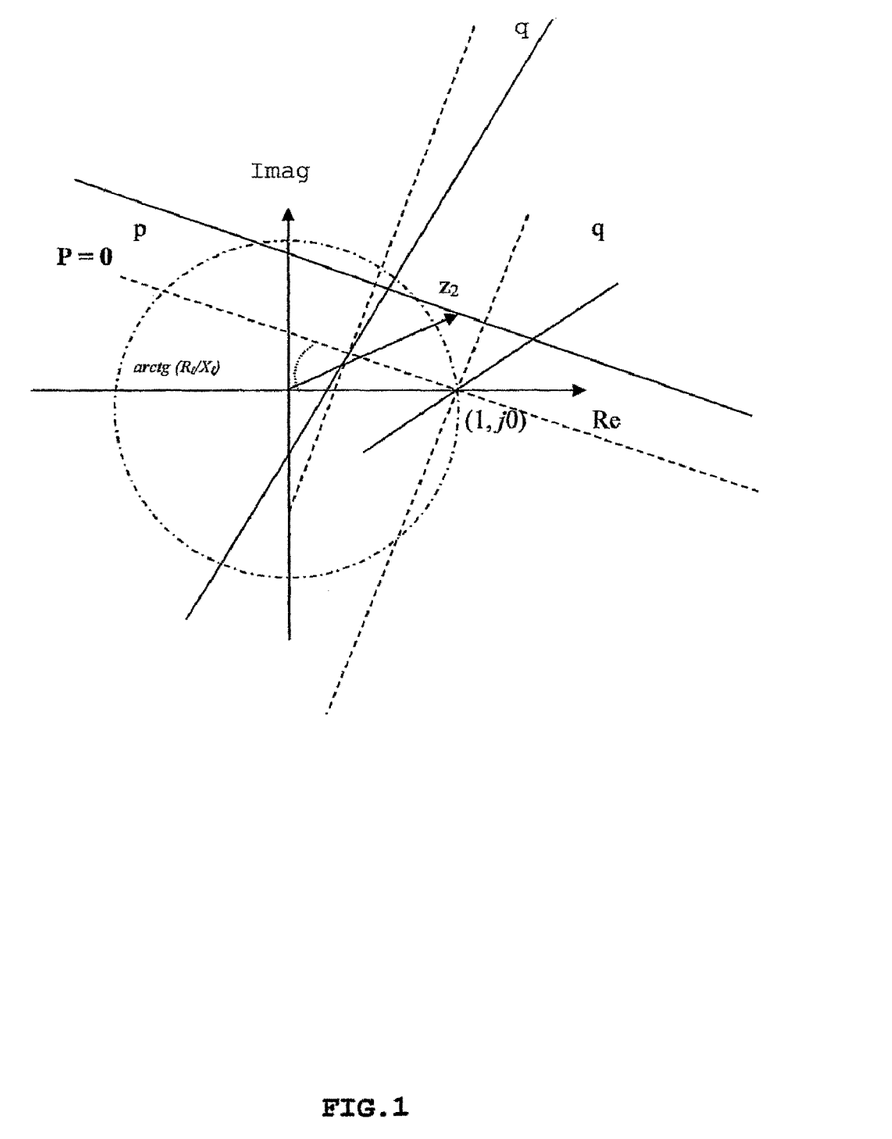
FIG. 1 illustrates an embodiment of the invention.

The invention optimises the reactive energy flow determined by the regime of exploration previewed at the Predictor-Corrector Abacus illustrated in FIG. 1.

The Predictor-Corrector Abacus is a representation in the complex plan of a situation where a specific load is supplied by an electrical energy to the Active Power P, and Reactive Power Q. The energy is submitted under a nominal voltage U in forced alternated sinusoidal condition at a frequency f.

What characterises this Abacus is the circumstance of considering the effect of the reactance and the resistance of longitudinal transmission lines, that is evident at the figure by the position of the angles of segment line that proliferate in the I and II quadrants of the Argand's complex plan, of the complex plan relative from the axis of the base. The effect of these parameters is presented in the synchronised rotation of segment line around the affix $z_1=1+j0$.

The affix $z_2$, represents the relations between the input and the output voltages. The unit radius of the circle corresponds to the points of the complex plan where $|z_2|=1$. The family of lines p, represents the geometric place of situations that correspond to the value of the active power P. However the lines q, characterise the situations that correspond to the Reactive Power Q.

The general equation for line p is $$y = -\frac{R_l}{X_l}x + \frac{R_l}{X_l} + \left(\frac{P}{U^2}\right)\left(\frac{Z_l^2}{X_l}\right)$$

On the other hand, lines q represents the situations corresponding to the reactive power Q.

The general equation of line q is $$y = \frac{X_l - R_l tg\varphi}{R_l + X_l tg\varphi}(x-1) + \left(\frac{Z_l^2}{R_l + X_l tg\varphi}\right)\omega C$$

Lines q turn by an angle $\phi$, corresponding to a phase difference between load voltage and current, starting from a point in the p line, with P=0.

The intersection of two lines p and q define the operating point and the voltage relation.

The mathematics model that presents the Abacus is defined by the following equation:

$$1+\overline{p}=\overline{m}=\sqrt{\frac{\left[1+\left(\frac{PR_l+QX_l}{U^2}\right)-\omega X_l C\right]^2 + }{\left[1+\left(\frac{PR_l-QX_l}{U^2}\right)-\omega R_l C\right]^2}} \; e^{j\left\{arctg\left[\frac{\left(\frac{PR_l-QX_l}{U^2}\right)-\omega R_l C}{1+\left(\frac{PR_l+QX_l}{U^2}\right)-\omega X_l C}\right]\right\}}$$

Where $\overline{m}$ the voltage ratio and $\overline{p}$ represents the losses factor.

The parameters that characterise the line are parameters distributed throughout their whole extension.

Centralizing the parameters of the distributed model in a compact coil, we obtain the representation of the reactance $X_l$ by concentrated parameters that consists the present transmission unit of this invention.

Thus, the transmitter unit resembles to a compact transmission line.

An additional advantage also becomes important, reported by the utilisation of the (co) sinusoidal signal. It consists on the focus effect which is obtained by the electromagnetic resonance phenomenon and that overcomes the high magnetic reluctance characterised by the long distance between the coil receptor and the transmitter unit.

Figure 2:
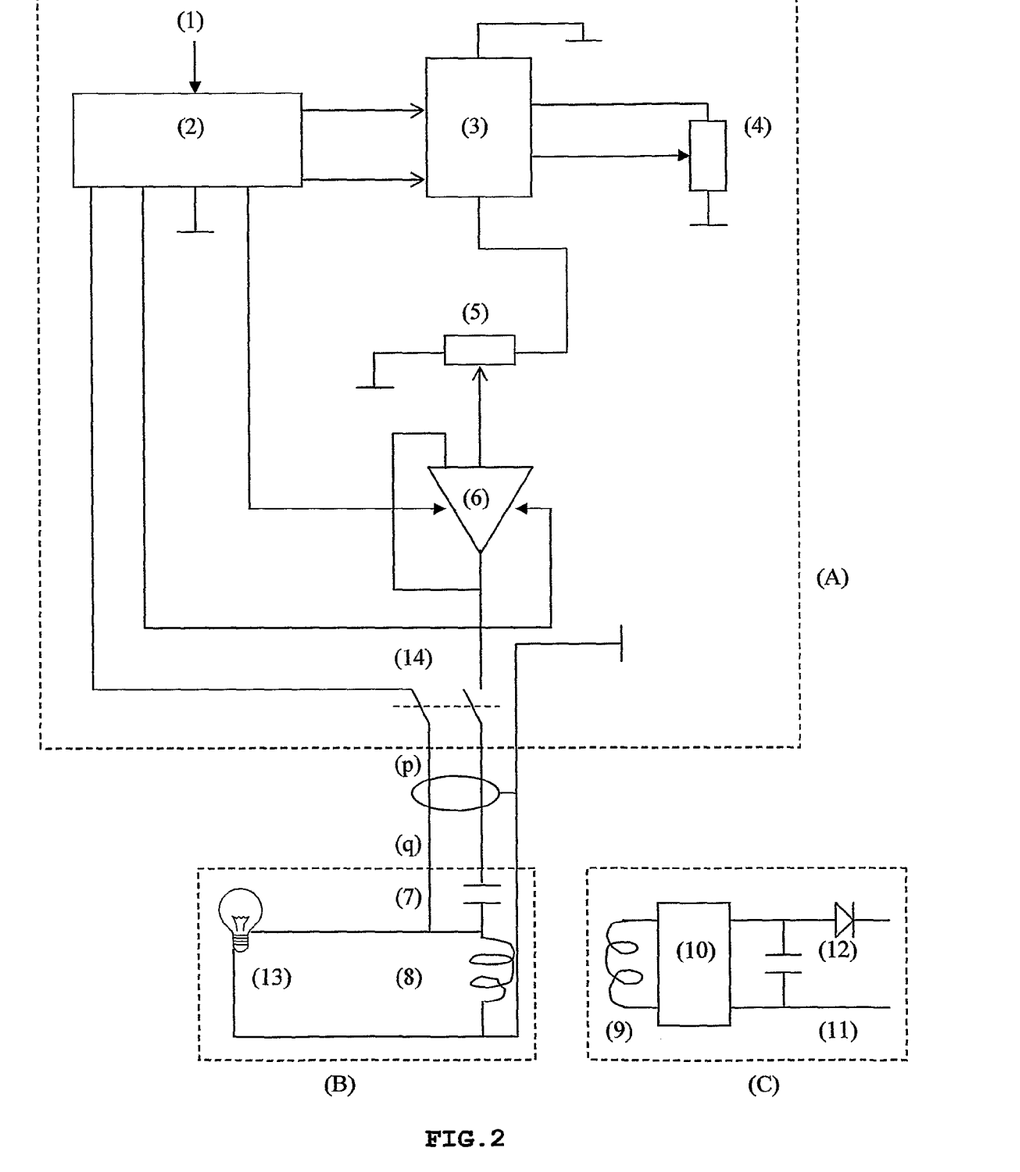
FIG. 2 illustrates a schematic diagram in accordance with an embodiment of the invention.

FIG. 2 represents the block diagram of the device. The energy supply is provided by the energy supply cable (1), by the alternating voltage from the energy public network, or by a direct current supply, the cigarette lighter plug of an automobile.

The converter (2) is used to supply the symmetrical voltages to the oscillator (3) and to the amplifier (6). Additionally, it supplies the inductor (8) of the transmitter unit (B), by the manual switch (14), in order to achieve a stationary magnetic field to instantly inhibit the pacemaker.

Potentiometer (4) adjust the frequency of the voltage controlled oscillator (VCO) (3), in order to minimize the reactive energy transfer, which can be visualized by the light sign (13).

The magnetic field intensity is adjusted through the potentiometer (5). Block (6) is the integrated hybrid amplifier that supplies the resonant network composed by the capacitor (7) and the primary coil (8), which constitutes the transmitter unit.

The magnetic field produced by this unit induces an alternating voltage in the coil terminals (9), which after rectification in the rectifier bridge (10), supplies the implant electronic circuit through the diode (11). This diode circumvents the implant battery from discharging in the equivalent leakage resistance.

The longitudinal resistance is majored by a value related to the skin effect, $R(\omega)$, determined by the depth of penetration $$\delta = \sqrt{\frac{2}{\omega\mu\sigma}}$$

and that characterises the dependence of the resistance behaviour on the frequency. The resistance varies from a value measured at direct current $R_0$, until $R(\omega)$.

On the same way the coil reactance depends on the frequency and also varies with magnetic reluctance, which is affected by the distance between coils. However, dispersion characterises a situation of maximum reluctance, which limits the circulating current in the compensation network.

Maxwell equation $\mathrm{div}\vec{B}=0$ characterises the dispersion of the field lines which close in the shortest path of the coil magnetic circuit. In this way, we identify a non-evasive behaviour (without leakage, control losses or limitation).

The control is efficient when $\overline{m}$ varies $75°<\theta<90°$, which and geometrically $\phi+\theta=90°$, corresponds to $0<\phi<15°$. The correspondent power factor, cos $\phi$, varies between 0.96 e 1.

The situation correspondent to $\theta=90°$, occurs at x=0. In this case, the ideal situation $\phi=0°$ e P=0, results from the equality between equations p e q the following:

$$y_P = -\frac{R_l}{X_l}x + \frac{R_l}{X_l} + \left(\frac{P}{U^2}\right)\left(\frac{Z_l^2}{X_l}\right) = -\frac{R_l}{X_l}x + \frac{R_l}{X_l}$$

-continued $$y_Q = \frac{X_l - R_l tg\varphi}{R_l + X_l tg\varphi}(x-1) + \left(\frac{Z_l^2}{R_l + X_l tg\varphi}\right)\omega C$$

$$= \frac{X_l}{R_l}(0-1) + \left(\frac{Z_l^2}{R_l}\right)\omega C$$

$$= -\frac{X_l}{R_l} + \left(\frac{Z_l^2}{R_l}\right)\omega C$$

$$y_P = y_Q \Leftrightarrow -\frac{R_l}{X_l}x + \frac{R_l}{X_l} = -\frac{X_l}{R_l} + \left(\frac{Z_l^2}{R_l}\right)\omega C \Leftrightarrow X_l = \frac{1}{\omega C} \Leftrightarrow L_l = \frac{1}{\omega^2 C}$$

The tuning frequency is obtained from $$\omega^2 = \frac{1}{L_l C} \Leftrightarrow f_0 = \frac{1}{2\pi\sqrt{L_l C}}$$

The situation when θ=75°, occurs when lines p e q are perpendicular and line q crosses origin, which means $$-\frac{R_l}{X_l}x = -\frac{R_l + X_l tg\varphi}{X_l - R_l tg\varphi} \Leftrightarrow \varphi = 0 \Rightarrow y_Q = \frac{X_l}{R_l}(x-1) + \ldots = \frac{X_l}{R_l}x$$

$$\therefore \arg\{\overline{m}\} = arctg\left(\frac{X_l}{R_l}\right) = argtg\left(\frac{\omega L_l}{r_0 + l\pi\Phi\delta}\right) = arctg\left(\frac{\omega L_l}{r_0 + l\pi\Phi\left(\frac{2}{\omega\mu\sigma}\right)}\right) \approx 75°$$

The induced voltage in the implanted coil is high when φ=0 and its value is given by $$U_1\left(\frac{n_2}{n_1}\right)\left(\frac{\omega L_l}{r_0 + l\pi\Phi\left(\frac{2}{\omega\mu\sigma}\right)}\right) = U_1\left(\frac{n_2}{n_1}\right)\left(\frac{X_l}{R_l}\right) = U_1\left(\frac{n_2}{n_1}\right)Q$$

where:

$U_1$, $(n_1/n_2)$ and Q, represents the RMS generator's voltage, the ratio of turns of the implanted/transmitter coils and the quality factor of the coil, respectively.

Figure 9:
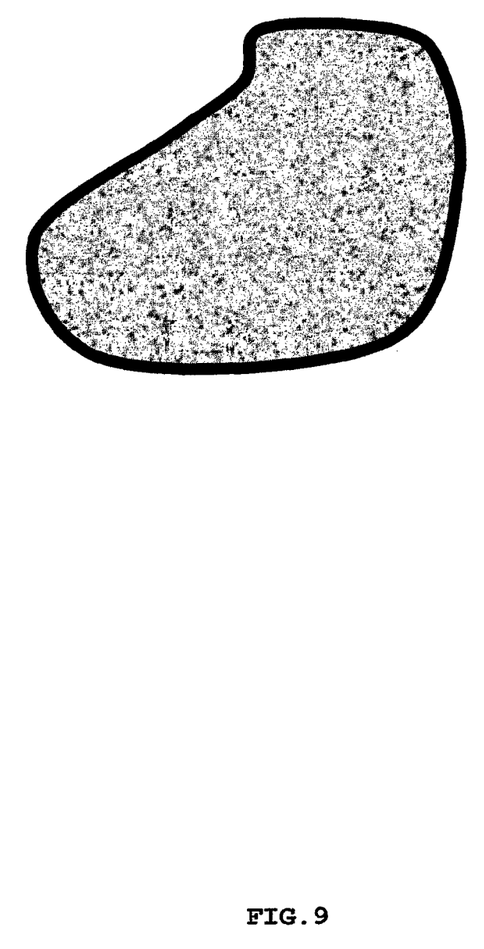
FIG. 9 illustrates an embodiment of the invention.
Figure 10:
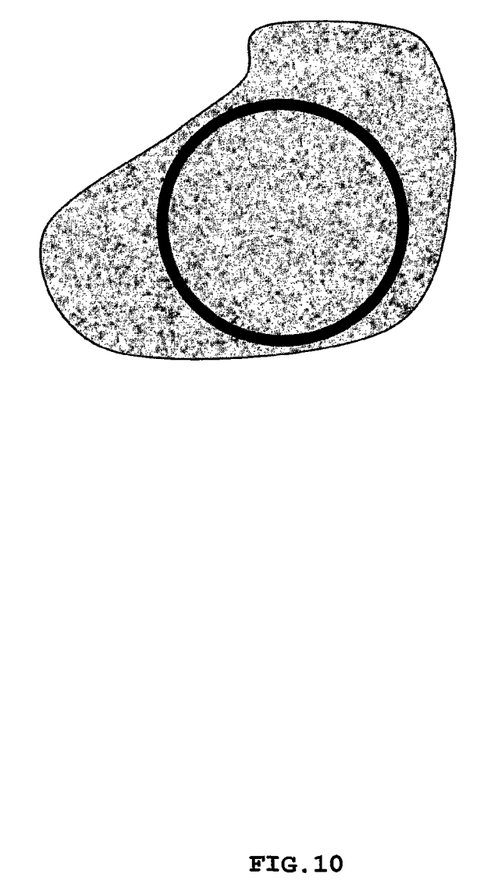
FIG. 10 illustrates an embodiment of the invention.

The implanted coil is located around the leakage line of the implant or in its interior, as depicted in FIGS. 9 and 10 respectively.

Figure 3:
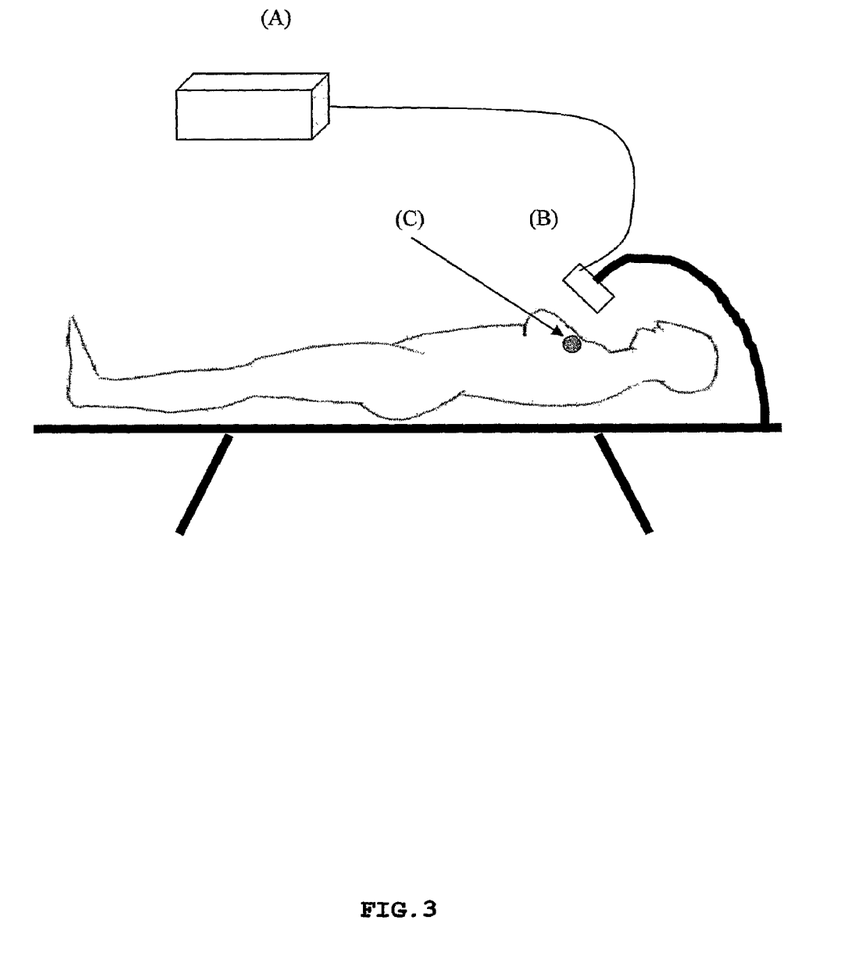
FIG. 3 illustrates an embodiment of the invention.

FIG. 3 indicates one of the possible applications of this invention. The generator unit is located in a fixed structure, like a table, shelf, etc. The transmitter unit should be located through an articulated arm with a support for example in a chair or even a bed. A flexible coaxial cable allows the connection between the generator and the transmitter unit, which by a simple but efficient location over the patient thorax, allows the energy transfer to the human body.

The position of switch (14) indicated in FIG. 2 determines if the magnetic field created by the transmitter coil is (co) sinusoidal, $B=B_{máx} \times sen(\omega t)$ or stationary, $B=B_{DC}$, respectively, if the coil current is supplied by the amplifier (6) or by the direct current supply (2). If the field is stationary, the transmitter unit works like a magnet, allowing the implant command in a way that it can suspend activity (magnetic mode); if the alternating field is selected, the implant is recharged.

Figure 4:
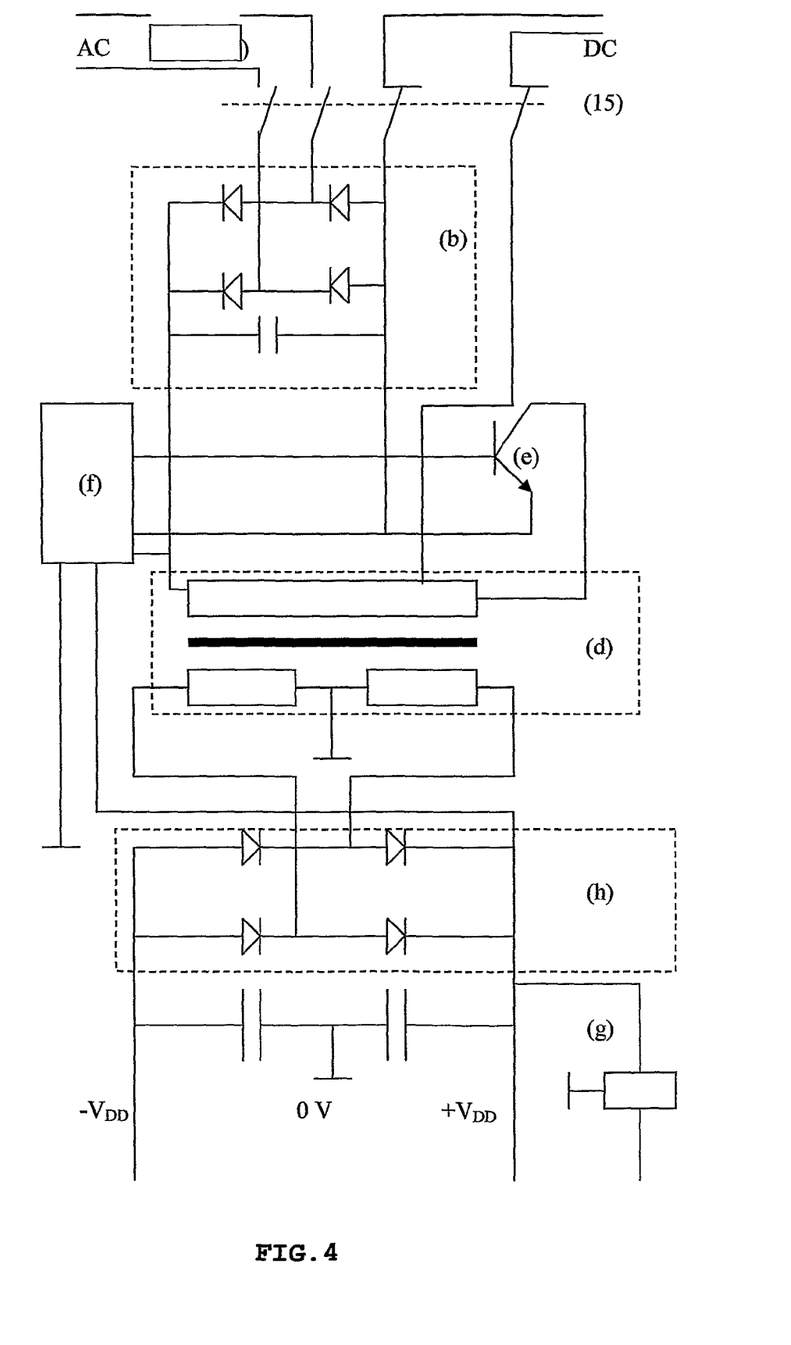
FIG. 4 illustrates a schematic diagram in accordance with an embodiment of the invention.

FIG. 4 represents the power supply scheme (2) indicated in FIG. 2, with the input and rectification blocks (a) e (b), the blocks (d), (e) e (f) that constitutes the flyback converter, the rectifying block (h), the filtering block (g) and the regulating block e current limiter (q) used to excite the transmitter coil through a direct current, which will create a stationary induced field $B=B_{DC}$, similar to the one produced by a permanent magnet.

Figure 5:
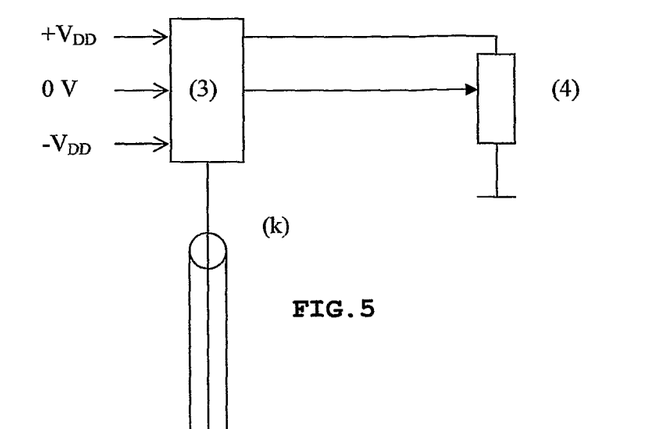
FIG. 5 and FIG. 6 illustrate a schematic diagram in accordance with an embodiment of the invention.

FIG. 5 represents the voltage controlled oscillator (3), identified in FIG. 2, and used to produce a (co) sinusoidal signal with frequency proportional to the control voltage, manually adjusted by the potentiometer (4). The mean value corresponds to the resonant frequency of the transmitter unit resonant network.

Figure 6:
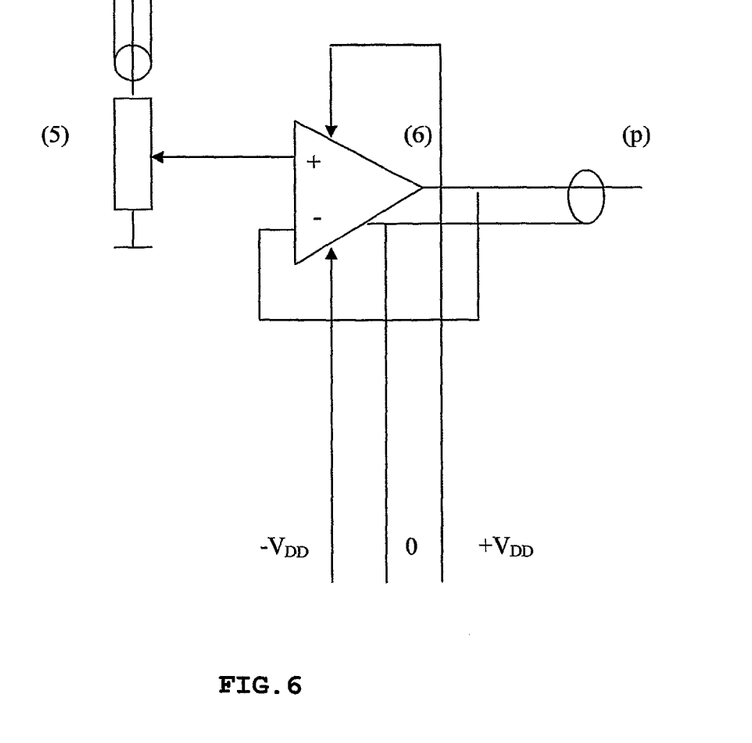

FIG. 6 represents the power amplifier with symmetric supply (6), which amplifies the signal generated at the voltage controlled oscillator (3) from FIG. 5, and let it available at the output plug (p).

Figure 7:
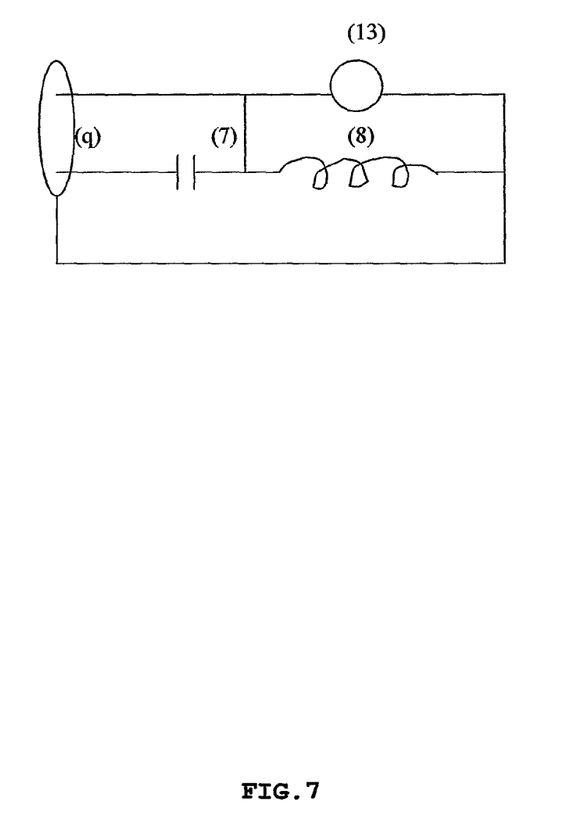
FIG. 7 illustrates a schematic diagram in accordance with an embodiment of the invention.

The scheme in FIG. 7 corresponds to the transmitter unit with a resonant capacitor (7), the coil (8), responsible for the magnetic field generation, a neon sign (13) and a plug (q) to connect to the generator unit (A) through plug (p), shown in FIG. 2.

Figure 8:
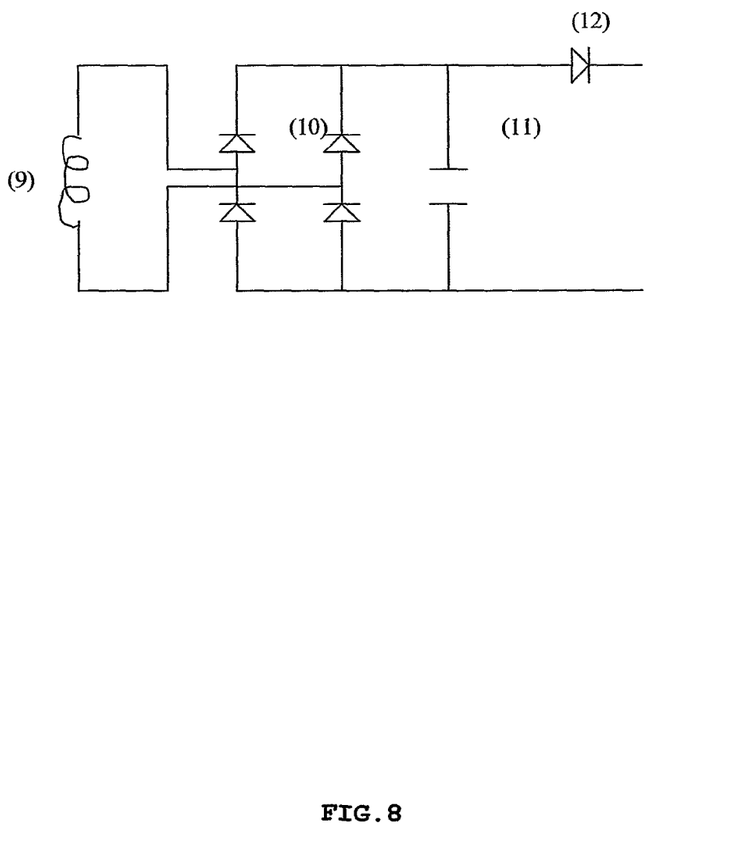
FIG. 8 illustrates a schematic diagram in accordance with an embodiment of the invention.

The implanted unit represented in FIG. 8 is constituted by the implanted coil (9) located in the periphery of the implant or in its interior and with the terminals connected to the rectifier bridge (10), which in turn are connected to the filter capacitor (11) e to the protection diode (12), which prevents the battery from discharging in the equivalent leakage resistance.

The assembly of the sensor coil (9) is suggested in FIGS. 9 and 10, respectively, by its location in the periphery or in the interior of the implant.

The invention claimed is:

1. A device for recharging the battery of cardiac implants comprising:
a generator (A) connectable and powerable by an AC or DC energy supply power source (1), at least first and second potentiometers (4, 5), a high power amplifier (6), a transmitter unit (B) comprising a resonant network with a capacitor (7) and a coil (8), said transmitter unit (B) adapted to produce a magnetic field that induces a voltage in a corresponding coil (9) of an implantable device (C), which is rectified by a bridge rectifier (10) and filtered by a capacitor, characterized in that said first potentiometer (4) is adapted to adjust the frequency of a (co)sinusoidal voltage controlled oscillator [(cosin VCO] (3) and said second potentiometer (5) is adapted to adjust the intensity and amplitude of the (co)sinusoidal voltage controlled oscillator [(co)din VCO] (3), the resulting signal being deliverable to said high power amplifier (6) which is connected through a coaxial cable to the transmitter unit (B) whose said coil (8) is a linear air core coil, said transmitter unit (B) being adapted for producing a (co)sinusoidal magnetic field which in turn indicates a (co)sinusoidal voltage in the said corresponding coil (9) of the implantable device (C).

2. A device for recharging the battery of cardiac implants according to claim 1, characterized in that the (co)sinusoidal voltage controlled oscillator [(co)sin VCO] (3) consists of an integrated circuit with a symmetric power supply that produces a (co)sinusoidal signal with a central oscillating frequency.

3. A device for recharging the battery of cardiac implants according to claim 1, characterised in that the said air core coil (8) and said capacitor (7) determine the maximum energy flux density generated by amplifier (6), without saturation phenomena thus, exhibiting linearity.

4. A device for recharging the battery of cardiac implants according to claim 1, characterised in that the said amplifier (6) is working at the class AB/B operation type.

5. A device for recharging the battery of cardiac implants according to claim 1, characterised in that the said first potentiometer adjusts the frequency of the said (co)sinusoidal voltage controlled oscillator [(co)sin VCO] (3) in order to achieve a resonant and optimal transfer condition.

6. A device for recharging the battery of cardiac implants according to claim 1, characterised in that the adjustment of the said second potentiometer (5) results in the adjustment of the magnetic field amplitude so as to obtain maximum focus effect whatever the depth of the said implantable device (C).

7. A device for recharging the battery of cardiac implants according to claim 1, characterised in that the said device has a stationary magnetic mode selected by the use of a switch (14) which permits the suspension of the activity of the said implantable device (C) or, alternatively providing the battery recharging mode with a (co)sinusoidal magnetic field.

* * * * *